United States Patent

De Nanteuil et al.

(10) Patent No.: US 6,302,837 B1
(45) Date of Patent: Oct. 16, 2001

(54) BENZOTHIOPHENE, BENZOFURAN AND INDOLE COMPOUNDS

(75) Inventors: Guillaume De Nanteuil, Suresnes; Christine Lila, Gif sur Yvette; Tony Verbeuren, Vernouillet; Alain Rupin, Savonnieres, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/687,308

(22) Filed: Oct. 13, 2000

(30) Foreign Application Priority Data

Oct. 15, 1999 (FR) .................................................. 99 12899

(51) Int. Cl.$^7$ ................... A61K 31/4436; A61K 31/381; C07D 409/06; C07D 409/14; A61P 7/02

(52) U.S. Cl. .......................... 574/337; 574/314; 574/333; 574/443; 574/418; 574/419; 574/470; 546/174; 546/256; 546/275.1; 546/281.1; 546/277.7; 546/284.1; 549/54; 549/406; 548/483; 548/484

(58) Field of Search .................................. 546/281.1, 256, 546/174, 275.1; 549/54; 514/337, 333, 314, 443

(56) References Cited

U.S. PATENT DOCUMENTS 6,048,875 * 4/2000 De Nanteuil ........................ 514/314

\* cited by examiner

*Primary Examiner*—Evelyn Mei Huang
(74) *Attorney, Agent, or Firm*—Hueschena and Sage; G. Patrick Sage

(57) ABSTRACT

A compound selected from those of formula (I):

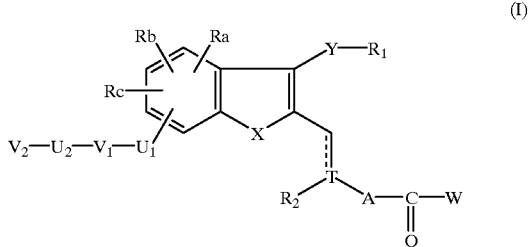

wherein:
- X represents oxygen, sulphur, or $NR_3$ wherein $R_3$ is as defined in the description,
- Y represents oxygen, sulphur, $NR_3$, or may represent single bond in certain cases,
- T represents nitrogen, carbon, or CH,
- A represents single bond, alkylene, arylene, cycloalkylene, heterocycloalkylene, heteroarylene, or $-SO_2-R_4-$ wherein $R_4$ is as defined in the description,
- W represents hydroxy, alkoxy, aryloxy, arylalkoxy, cycloalkyloxy, heterocycloalkyloxy or heteroaryloxy, or hydroxyamino,
- $U_1$ represents hetero, or alkylene wherein one or more of carbon may optionally be replaced by one or more hetero atoms,
- $V_1$ represents arylene, heteroarylene, or heterocycloalkylene,
- $U_2$ represents single bond, hetero or alkylene wherein one or more carbon may optionally be replaced by one or more hetero atoms,
- $V_2$ represents aryl, heteroaryl, or heterocycloalkyl,
- Ra, Rb, Rc, which may be identical or different, each independently of the others represents a group as defined in the description,
- $R_1$ represents aryl substituted by from one to five substituents, 1,3-dihydro-2H-indol-2-one, 3,4-dihydro-2(1H)-quinolinone, 1-hydroxy-2(1H)-pyridinone group, or heteroaryl,
- $R_2$ represents halogen, alkyl, aryl, arylalkyl, cycloalkyl, heterocycloalkyl, heterocycloalkylalkyl, heteroaryl, or heteroarylalkyl, its isomers, and pharmaceutically-acceptable acid or base addition salts thereof, and medicinal products containing the same which are useful as inhibitors of PAI-1 in the treatment of thrombosis, pathologies for which the origin is thrombosis, or pathologies causing an increase in risk of thrombosis.

18 Claims, No Drawings

BENZOTHIOPHENE, BENZOFURAN AND INDOLE COMPOUNDS

FIELD OF THE INVENTION

The present invention relates to new benzothiophene, benzofuran and indole compounds, and to pharmaceutical compositions containing them. These new compounds are useful for their therapeutic activity in the field of fibrinolysis and thrombosis, by virtue of their property of inhibiting the activity of PAI-1.

PAI-1 is a powerful inhibitor of plasminogen activators (tissue plasminogen activator and urokinase). In vitro and in vivo, it causes inhibition of the breakdown of the fibrinous clots, formed by the action of thrombin on fibrinogen. A number of epidemiological studies have shown that, in man, high levels of PAI-1 are associated with more frequent occurrence of thromboembolic disorders. Moreover, in experimental models of thrombosis and thrombolysis, inhibition of the activity of PAI-1 by anti-PAI-1 monoclonal antibodies reduces the incidence of thromboses or reocclusions. The therapeutic value of molecules having the property of inhibiting the activity of PAI-1 in the fibrinous clot that has been formed or that is in the process of being formed is thus to enable it to be broken down at an early stage before it is complexed with Factor XIIIa and thus to reduce the incidence of thromboembolic accidents in patients having high levels of PAI-1. Such compounds are therapeutically valuable in all pathologies for which the origin is thrombosis (such as myocardial infarction, angina, intermittent claudication, cerebral vascular accidents, deep vein thrombosis, or pulmonary embolism) and in pathologies in which thrombotic risks are increased (such as hypertension, hypercholesterolaemia, diabetes, obesity, genetic coagulation anomalies (Factor V Leiden, deficit in proteins C and S) or acquired coagulation anomalies).

The compounds of the present invention, in addition to being new, have proved to be more powerful PAI-1 inhibitors than those described in the literature, which thus makes them potentially useful in the treatment of thrombosis, pathologies the origin of which is thrombosis and pathologies causing an increase in thrombotic risks.

PRIOR ART OF THE INVENTION

A number of antithrombotics have been described in the literature. This is the case, more, especially, of the compounds described in Patent Specifications WO 97/45424, WO 94/08962, EP 540 051 and GB 2225012.

DETAILED DESCRIPTION OF THE INVENTION

More specifically, the present invention relates to compounds of formula (I):

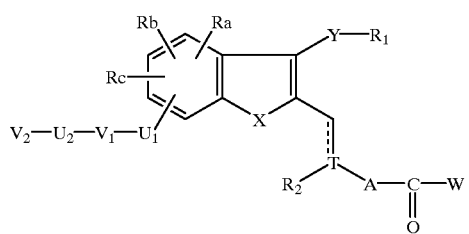

wherein:

X represents an oxygen atom, a sulphur atom, or an $NR_3$ group wherein $R_3$ represents a hydrogen atom, a linear or branched $(C_1-C_6)$alkyl group, a linear or branched $(C_1-C_6)$acyl group, an aryl group, an aryl-$(C_1-C_6)$alkyl group in which the alkyl moiety is linear or branched, or a heteroaryl-$(C_1-C_6)$alkyl group in which the alkyl moiety is linear or branched, Y represents an oxygen atom, a sulphur atom or an $NR_3$ group, the $R_3$ group being as defined above, or may represent a single bond when X represents an $NR'_3$ group wherein $R'_3$ represents a heteroaryl-$(C_1-C_6)$alkyl group in which the alkyl moiety is linear or branched, T represents a nitrogen atom when the bond that links it to the adjacent carbon atom is single (—), or a carbon atom or a CH group depending on whether the bond that links it to the adjacent carbon atom is single (—) or double (═), A represents a single bond or a group selected from $(C_1-C_6)$alkylene (optionally substituted by one or more linear or branched $(C_1-C_6)$alkyl groups, aryl groups, aryl-$(C_1-C_6)$alkyl groups in which the alkyl moiety is linear or branched, cycloalkyl groups, heterocycloalkyl groups or heteroaryl groups), arylene, cycloalkylene, heterocycloalkylene, heteroarylene and an —$SO_2$—$R_4$— group (the $SO_2$ moiety being linked to T) wherein $R_4$ represents a group selected from linear or branched $(C_1-C_6)$alkylene, arylene, aryl-$(C_1-C_6)$alkylene in which the alkylene moiety is linear or branched, cycloalkylene, heterocycloalkylene and heteroarylene, W represents a group selected from hydroxy, linear or branched $(C_1-C_6)$alkoxy, aryloxy, aryl-$(C_1-C_6)$alkoxy in which the alkoxy moiety is linear or branched, cycloalkyloxy, heterocycloalkyloxy, heteroaryloxy, amino (which may itself be substituted by one or two identical or different groups each independently of the other selected from linear or branched $(C_1-C_6)$alkyl, aryl, aryl-$(C_1-C_6)$alkyl in which the alkyl moiety is linear or branched, and cycloalkyl) and hydroxyamino, $U_1$ represents an oxygen atom, a sulphur atom or a linear or branched $(C_1-C_6)$alkylene chain wherein one or more of the carbon atoms may optionally be replaced by one or more hetero atoms selected from oxygen, nitrogen and sulphur, the said alkylene chain being optionally substituted by one or more identical or different groups selected from halogen, hydroxy, linear or branched $(C_1-C_6)$alkyl and linear or branched $(C_1-C_6)$alkoxy, $V_1$ represents an arylene, heteroarylene or heterocycloalkylene group, $U_2$ represents a single bond, an oxygen, nitrogen or sulphur atom or a linear or branched $(C_1-C_6)$alkylene chain wherein one or more carbon atoms may optionally be replaced by one or more identical or different groups selected from oxygen, sulphur and nitrogen atoms (a nitrogen atom being substituted by a group selected from hydrogen and linear or branched $(C_1-C_6)$ alkyl) and an $SO_2$ group, $V_2$ represents an aryl, heteroaryl or heterocycloalkyl group, Ra, Rb and Rc, which may be identical or different, each independently of the others represents a group selected from:
hydrogen, halogen,
hydroxy, cyano, nitro,
linear or branched $(C_1-C_6)$alkyl, linear or branched $(C_1-C_6)$alkoxy, linear or branched $(C_1-C_6)$acyl, carboxy, linear or branched ($C_1$–$C_6$)alkoxycarbonyl, linear or branched ($C_1$–$C_6$)trihaloalkyl, amino (optionally substituted by one or two groups, which may be identical or different, each independently of the other selected from linear or branched ($C_1$–$C_6$)alkyl, aryl and aryl-($C_1$–$C_6$)alkyl in which the alkyl moiety is linear or branched), aryloxy, aryl-($C_1$–$C_6$)alkoxy in which the alkoxy moiety is linear or branched, heteroaryloxy, heteroaryl-($C_1$–$C_6$)alkoxy in which the alkoxy moiety is linear or branched, and a group of formula —$U_1$—$V_1$—$U_2$—$V_2$ wherein $U_1$, $U_2$, $V_1$ and $V_2$ are as defined hereinbefore, or two of them together form a methylenedioxy or ethylenedioxy group (each of those groups being optionally substituted by one or two linear or branched ($C_1$–$C_6$)alkyl groups, aryl groups or aryl-($C_1$–$C_6$)alkyl groups in which the alkyl moiety is linear or branched), $R_1$ represents:

an aryl group substituted by from one to five identical or different substituents each independently of the others selected from halogen, hydroxy, cyano, nitro, carboxy, linear or branched ($C_1$–$C_6$)alkyl, linear or branched ($C_1$–$C_6$)alkoxy, linear or branched ($C_1$–$C_6$) acyl, linear or branched ($C_1$–$C_6$)alkoxycarbonyl, linear or branched ($C_1$–$C_6$)trihaloalkyl (optionally substituted by a hydroxy group), linear or branched ($C_1$–$C_6$)trihaloalkoxy, amino (optionally substituted by one or two linear or branched ($C_1$–$C_6$)alkyl groups, one of which alkyl groups may be optionally substituted by a group selected from amino, linear or branched ($C_1$–$C_6$)alkylamino and di-($C_1$–$C_6$)alkylamino in which the alkyl moieties are each linear or branched), amino-($C_1$–$C_6$)alkoxy (in which the alkoxy moiety is linear or branched and the amino moiety is optionally substituted by one or two, identical or different, linear or branched ($C_1$–$C_6$) alkyl groups), ($C_1$–$C_6$)alkoxycarbonyl($C_1$–$C_6$)alkyl in which the alkoxy and alkyl moieties are each linear or branched, linear or branched ($C_1$–$C_6$)-alkylcarbonylamino, aryl-($C_1$–$C_6$)alkyl in which the alkyl moiety is linear or branched, aryloxy, aryl-($C_1$–$C_6$)alkoxy in which the alkoxy moiety is linear or branched, arylamino, aryl-($C_1$–$C_6$)alkylamino in which the alkyl moiety is linear or branched, arylsulphanyl, aryl-($C_1$–$C_6$)alkylsulphanyl in which the alkyl moiety is linear or branched, heteroaryl, heteroaryl-($C_1$–$C_6$)alkyl in which the alkyl moiety is linear or branched, heteroaryloxy, heteroaryl-($C_1$–$C_6$)alkoxy in which the alkoxy moiety is linear or branched, heteroarylamino, heteroaryl-($C_1$–$C_6$)alkylamino in which the alkyl moiety is linear or branched, heteroarylsulphanyl, heteroaryl-($C_1$–$C_6$)alkylsulphanyl in which the alkyl moiety is linear or branched, a 1,3-dihydro-2H-indol-2-one, 3,4-dihydro-2(1H)-quinolinone or 1-hydroxy-2(1H)-pyridinone group, or an optionally substituted heteroaryl group, $R_2$ represents a group selected from a hydrogen atom, a linear or branched ($C_1$–$C_6$)alkyl group, an aryl group, an aryl-($C_1$–$C_6$)alkyl group in which the alkyl moiety is linear or branched, a cycloalkyl group, a heterocycloalkyl group, a heterocycloalkyl-($C_1$–$C_6$)alkyl group in which the alkyl moiety is linear or branched, a heteroaryl group and a heteroaryl-($C_1$–$C_6$)alkyl group in which the alkyl moiety is linear or branched, wherein:

an aryl group is understood to be a phenyl, biphenyl, naphthyl, tetrahydronaphthyl or dihydronaphthyl group, each of those groups being optionally substituted by one or more identical or different groups selected from halogen, hydroxy, cyano, nitro, linear or branched ($C_1$–$C_6$)alkyl (optionally substituted by one or more groups selected from hydroxy, amino and mono- or di-($C_1$–$C_6$)alkylamino in which the alkyl moieties are each linear or branched), linear or branched ($C_1$–$C_6$)trihaloalkyl, linear or branched ($C_1$–$C_6$)alkoxy, aryloxy, linear or branched ($C_1$–$C_6$) acyl, carboxy, linear or branched ($C_1$–$C_6$) alkoxycarbonyl and amino (amino being optionally substituted by one or two identical or different linear or branched ($C_1$–$C_6$)alkyl groups), a cycloalkyl group is understood to be a mono- or bi-cyclic group containing from 3 to 8 carbon atoms, heterocycloalkyl is understood to be a mono- or bi-cyclic, saturated or unsaturated group, of non-aromatic character, having from 5 to 12 ring members containing one, two or three identical or different hetero atoms selected from oxygen, nitrogen and sulphur, it being understood that the heterocycloalkyl may be optionally substituted by one or more identical or different groups selected from halogen, hydroxy, linear or branched ($C_1$–$C_6$)alkyl, linear or branched ($C_1$–$C_6$)trihaloalkyl, linear or branched ($C_1$–$C_6$)alkoxy, aryloxy, aryl-($C_1$–$C_6$) alkoxy in which the alkoxy moiety is linear or branched, amino (optionally substituted by one or two linear or branched ($C_1$–$C_6$)alkyl groups), linear or branched ($C_1$–$C_6$)acyl, linear or branched ($C_1$–$C_6$) alkoxycarbonyl, nitro groups and oxo, heteroaryl is understood to be a mono- or bi-cyclic heterocycloalkyl as defined hereinbefore, at least one of the rings of which has an aromatic character, it being possible for the hetero atom(s) to be located, in the case of a bicyclic system, on the ring having an aromatic character or on the partially unsaturated ring, it being understood that the heteroaryl group may be optionally substituted by one or more identical or different groups as defined for the substituents of heterocycloalkyl, their isomers and addition salts thereof with a pharmaceutically acceptable acid or base.

Among the pharmaceutically acceptable acids there may mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc..

Among the pharmaceutically acceptable bases there may mentioned, without implying any limitation, sodium hydroxide, potassium hydroxide, triethylamine, tert-butylamine etc..

Among the heterocycloalkyls there may be mentioned, without implying any limitation, heterocycloalkyls such as piperidine, piperazine and morpholine.

Among the heteroaryls there may be mentioned, without implying any limitation, heteroaryls such as pyridine, pyrimidine, quinoline, isoquinoline, 1,3-dihydro-2H-pyrrolopyridin-2-one, 3H-imidazopyridine, 1H-pyrrolopyridine, 1,2,3,4-tetrahydronaphthopyridine and 2,3-dihydro-1H-pyrrolopyridine.

Preferred compounds of the invention are those wherein X represents a sulphur atom or an $NR_3$ group wherein $R_3$ is as defined for formula (I).

Preferred compounds of the invention are those wherein Y represents an oxygen atom.

The $R_1$ substituents preferred according to the invention are groups selected from phenyl optionally substituted by a group as defined for formula (I), optionally substituted quinolyl and optionally substituted pyridyl.

The $R_2$ substituents preferred according to the invention are groups selected from aryl and heteroaryl, each of those groups being optionally substituted. According to an advantageous embodiment, the preferred $R_2$ substituent is the pyridyl group.

The —$U_1$—$V_1$—$U_2$—$V_2$ substituents preferred according to the invention are the substituents wherein $U_1$ represents a linear ($C_1$–$C_4$)alkylene chain wherein one of the carbon atoms is replaced by an oxygen atom, $V_1$ represents an arylene group, $U_2$ represents a single bond and $V_2$ represents an aryl group optionally substituted by one of the groups as defined for formula (I).

Especially advantageously, the preferred —$U_1$—$V_1$—$U_2$—$V_2$ substituent is the [1,1'-biphenyl]-4-ylmethoxy grouping.

According to a preferred embodiment of the invention, preferred compounds are those wherein one of the groups Ra, Rb, or Rc represents a grouping of formula —$U_1$—$V_1$—$U_2$—$V_2$ as defined for formula (I).

According to an advantageous embodiment of the invention, preferred compounds are those wherein X represents a sulphur atom and Y represents an oxygen atom.

According to an especially advantageous embodiment of the invention, preferred compounds are those wherein:

X represents a sulphur atom,

Y represents an oxygen atom, $R_1$ represents an optionally substituted phenyl group or an optionally substituted pyridyl group, A represents a single bond when T represents a carbon atom or a CH group.

According to a third advantageous embodiment, preferred compounds of the invention are those wherein:

X represents a sulphur atom,

Y represents an oxygen atom, $R_1$ represents a phenyl group optionally substituted by a group as defined for formula (I), A represents an alkylene group (optionally substituted by a linear or branched ($C_1$–$C_6$)alkyl group, an aryl group or by an aryl-($C_1$–$C_6$)alkyl group in which the alkyl moiety is linear or branched) or an arylene group when T represents a nitrogen atom.

According to a fourth advantageous embodiment, preferred compounds of the invention are the compounds of formula (II):

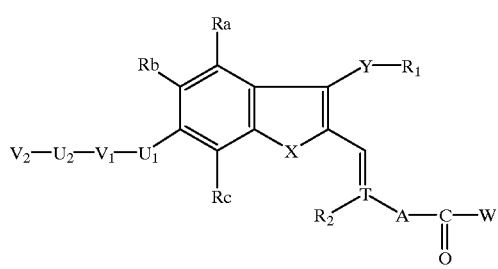

(II)

wherein:

X represents a sulphur atom,

Y represents an oxygen atom, $R_1$ represents an optionally substituted phenyl group or an optionally substituted pyridyl group, A represents a single bond, T represents a carbon atom, Ra and Rc each represents a hydrogen atom, $U_1$ represents a linear ($C_1$–$C_4$)alkylenoxy chain, $V_1$ represents an arylene group, $U_2$ represents a single bond, $V_2$ represents an aryl group, Rb represents a $U_1$—$V_1$—$U_2$—$V_2$ grouping as defined hereinbefore, $R_2$ represents a heteroaryl group, W represents a group as defined for formula (I).

In a very advantageous form, preferred compounds of the invention are the compounds of formula (I bis) wherein Rb and —$U_1$—$V_1$—$U_2$—$V_2$ each represent a [1,1'-biphenyl]-4-ylmethoxy grouping.

In another very advantageous form, preferred compounds of the invention are the compounds of formula (I bis) wherein $R_2$ represents a pyridyl group.

In a third very advantageous form, preferred compounds of the invention are the compounds of formula (I bis) wherein $R_1$ represents:

a phenyl group optionally substituted by from one to three groups selected from halogen, linear or branched ($C_1$–$C_6$)alkyl, heteroaryl, heteroaryl-($C_1$–$C_6$)alkoxy in which the alkoxy moiety is linear or branched, linear or branched ($C_1$–$C_6$)alkoxy, amino and linear or branched amino-($C_1$–$C_6$)alkoxy, it being possible for the amino moiety to be substituted (in each of those two groups) by one or two identical or different linear or branched ($C_1$–$C_6$)alkyl groups, or a heteroaryl group selected from pyridyl and quinolyl optionally substituted by a halogen atom or a linear or branched ($C_1$–$C_6$)alkyl group.

Preferred compounds according to the invention are:

(E)-3-[5,6-bis([1,1'-biphenyl]-4-ylmethoxy)-3-(4-chlorophenoxy)benzo[b]thiophen-2-yl]-2-(4-pyridyl)-2-propenoic acid, ethyl (E)-3-[5,6-bis-([1,1'-biphenyl]-4-ylmethoxy)-3-(4-chlorophenoxy)benzo[b]thiophen-2-yl]-2-(4-pyridyl)-2-propenoate, (E)-3-[5,6-bis-([1,1'-biphenyl]-4-ylmethoxy)-3-(3-pyridyloxy)benzo[b]thiophen-2-yl]-2-(4-pyridyl)-2-propenoic acid, 3-(E)-{5,6-bis-([1,1'-biphenyl]-4-ylmethoxy)-3-[6-(methyl)pyridyl-3-oxy]benzo[b]thiophen-2-yl}-2-(4-pyridyl)-2-propenoic acid, 3-(E)-[5,6-bis-([1,1'-biphenyl]-4-ylmethoxy)-3-(6-quinolyloxy)benzo[b]thiophen-2-yl]-2-(4-pyridyl)-2-propenoic acid, (E)-3-[5,6-bis-([1,1'-biphenyl]-2-ylmethoxy)-3-(4-chlorophenoxy)benzo[b]thiophen-2-yl]-2-(4-pyridyl)-2-propenoic acid, (E)-3-[5,6-bis([1,1'-biphenyl]-3-ylmethoxy)-3-(4-chlorophenoxy)benzo[b]thiophen-2]-2-(4-pyridyl)-2-propenoic acid, (E)-3-[5,6-bis([1,1'-biphenyl]-4-ylmethoxy)-3-(4-chloro-3-fluorophenoxy)benzo[b]thiophen-2-yl]-2-(4-pyridyl)-2-propenoic acid, (E)-3-[5,6-bis([1,1'-biphenyl]-4-ylmethoxy)-3-(4-chloro-3,5-dimethylphenoxy)benzo[b]-thiophen-2-yl]-2-(4-pyridyl)-2-propenoic acid, (E)-3-[5,6-bis([1,1'-biphenyl]-4-ylmethoxy)-3-(4-chloro-3-methylphenoxy)benzo[b]thiophen-2-yl]-2-(4-pyridyl)-2-propenoic acid, (E)-3-{5,6-bis([1,1'-biphenyl]-4-ylmethoxy)-3-[4-(4-pyridyloxy)phenoxy]benzo[b]thiophen-2-yl}-2-(4-pyridyl)-2-propenoic acid, (E)-3-{5,6-bis([1,1'-biphenyl]-4-ylmethoxy)-3-[4-(1H-imidazol-1-yl)phenoxy]benzo[b]-thiophen-2-yl}-2-(4-pyridyl)-2-propenoic acid, (E)-3-[5,6-bis([1,1'-biphenyl]-4-ylmethoxy)-3-phenoxybenzo[b]thiophen-2-yl]-2-(4-pyridyl)-2-propenoic acid, (E)-3-[5,6-bis([1,1'-biphenyl]-4-ylmethoxy)-3-(3-fluorophenoxy)benzo[b]thiophen-2-yl]-2-(4 4-pyridyl)-2-propenoic acid, (E)-3-[5,6-bis([1,1'-biphenyl]-4-ylmethoxy)-3-(3,4-difluorophenoxy)benzo[b]-thiophen-2-yl]-2-(4-pyridyl)-2-propenoic acid, (E)-3-{5,6-bis([1,1'-biphenyl]-4-ylmethoxy)-3-[(6-chloro-3-pyridyl)oxy]benzo[b]thiophen-2-yl}-2-(4-pyridyl)-2-propenoic acid.

The isomers, as well as the addition salts with a pharmaceutically acceptable acid or base, of the preferred compounds form an integral part of the invention.

The invention relates also to a process for the preparation of compounds of formula (I), which process is characterised in that there is used as starting material a compound of formula (II):

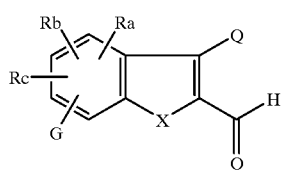

(II)

wherein Ra, Rb, Rc and X are as defined for formula (I), G represents a hydroxy group protected by a protecting group conventionally used in organic synthesis and Q represents a halogen atom or a hydroxy group and, preferably, Q represents a halogen atom when X represents a sulphur atom or an $NR_3$ group wherein $R_3$ is as defined for formula (I) and Q represents a hydroxy group when X represents an oxygen atom, which compound of formula (II) is reacted, under basic conditions,
when Q represents a halogen atom,
with a compound of formula (III),

(III)

wherein $R_1$ is as defined for formula (I) and $Y_1$ represents an oxygen atom, a sulphur atom or an $NR_3$ group wherein $R_3$ is as defined for formula (I), to yield the compounds of formula (IV/a):

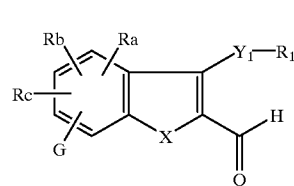

(IV/a)

wherein Ra, Rb, Rc, G, $R_1$, X and Y, are as defined hereinbefore, or with a compound of formula (V):

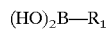

(V)

wherein $R_1$ is as defined for formula (I),
to yield the compounds of formula (IV/b):

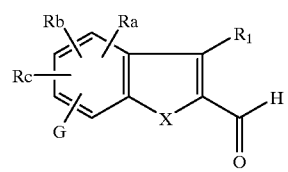

(IV/b)

wherein Ra, Rb, Rc, G and $R_1$ are as defined hereinbefore and $X_1$ represents an $NR_3$ group wherein $R_3$ represents a heteroaryl-$(C_1-C_6)$alkyl group in which the alkyl moiety is linaear or branched, or, when Q represents a hydroxy group, with a compound of formula (VI),

(VI)

wherein Hal represents a halogen atom and $R_1$ is as defined hereinbefore, to yield the compounds of formula (IV/c):

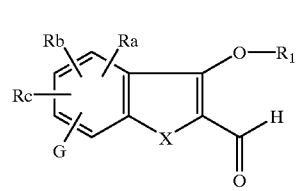

(IV/c)

wherein Ra, Rb, Rc, G, X and $R_1$ are as defined hereinbefore, the totality of the compounds of formulae (IV/a), (IV/b) and (IV/c) constituting the compounds of formula (IV):

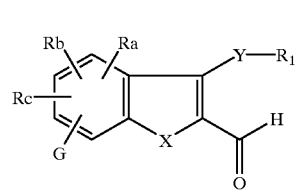

(IV)

wherein Ra, Rb, Rc, G, $R_1$, X and Y are as defined for formula (I), which compounds of formula (IV):
are condensed, in the presence of acetic anhydride, with a compound of formula (VII),

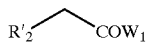
(VII)

wherein R'$_2$ has the same definition as R$_2$ for formula (I), with the exception that R'$_2$ cannot represent a hydrogen atom, and W$_1$ represents a group selected from linear or branched (C$_1$–C$_6$)alkoxy, aryloxy, aryl-(C$_1$–C$_6$)alkoxy in which the alkoxy moiety is linear or branched, cycloalkyloxy, heterocycloalkoxy, heteroaryloxy and an amino group (which is itself optionally substituted by one or two identical or different groups each independently of the other selected from linear or branched (C$_1$–C$_6$)alkyl, aryl, aryl-(C$_1$–C$_6$)alkyl in which the alkyl moiety is linear or branched, and cycloalkyl),
to yield the compounds of formula (VIII):

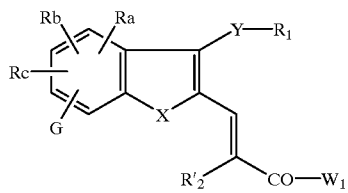
(VIII)

wherein Ra, Rb, Rc, G, R$_1$, R'$_2$, X, Y and W$_1$ are as defined hereinbefore,
the hydroxy function of which compounds of formula (VII) is deprotected under conventional conditions of organic synthesis, and which are then reacted in a basic medium with a compound of formula (IX):

(IX)

wherein U$_1$, V$_1$, U$_2$ and V$_2$ are as defined for formula (I) and Hal represents a halogen atom, to yield the compounds of formula (I/a), a particular case of the compounds of formula (I):

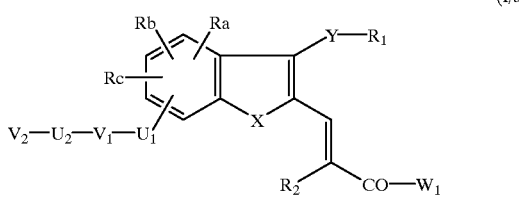
(I/a)

wherein Ra, Rb, Rc, U$_1$, V$_1$, U$_2$, V$_2$, R$_1$, R'$_2$, X, Y and W$_1$ are as defined hereinbefore,
which compounds of formula (I/a) are, if desired, subjected:
either to conditions of catalytic hydrogenation, in the presence of palladium, to yield the compounds of formula (I/b), a particular case of the compounds of formula (I):

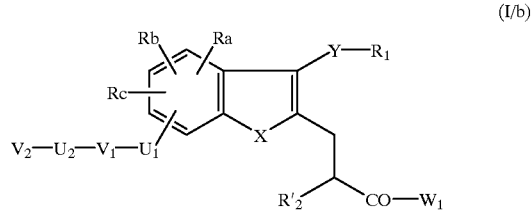
(I/b)

wherein Ra, Rb, Rc, U$_1$, V$_1$, U$_2$, V$_2$, R$_1$, R'$_2$, X, Y and W$_1$ are as defined hereinbefore,
or to conditions of hydrolysis, in a basic medium, to yield the compounds of formula (I/c), a particular case of the compounds of formula (I):

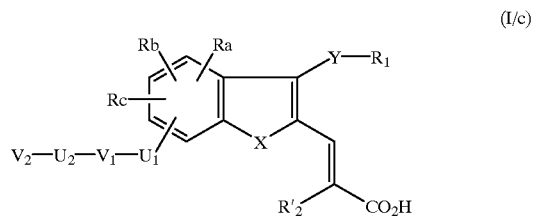
(I/c)

wherein Ra, Rb, Rc, U$_1$, V$_1$, U$_2$, V$_2$, R$_1$, R'$_2$, X and Y are as defined hereinbefore,
the double bond of which compounds of formula (I/c) is, if desired, reduced by catalytic hydrogenation to yield the compounds of formula (I/d), a particular case of the compounds of formula (I):

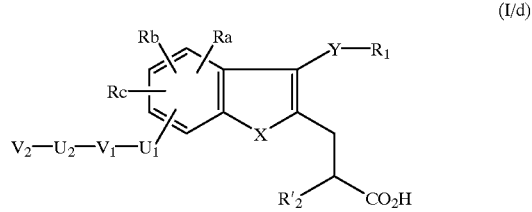
(I/d)

wherein Ra, Rb, Rc, U$_1$, V$_1$, U$_2$, V$_2$, R$_1$, R'$_2$, X and Y are as defined hereinbefore,
or are subjected to the action of a phosphorus ylid of formula (X),

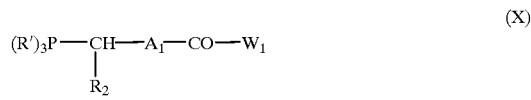
(X)

wherein R' represents a linear or branched (C$_1$–C$_6$) alkyl group or a phenyl group, R$_2$ is as defined for formula (I), W$_1$ is as defined hereinbefore and A$_1$ represents a single bond, an alkylene group (optionally substituted by one or more groups selected from linear or branched (C$_1$–C$_6$)alkyl, aryl, aryl-(C$_1$–C$_6$)alkyl in which the alkyl moiety is linear or branched, cycloalkyl, heterocycloalkyl and heteroaxyl), an arylene group, a cycloalkylene group, a heterocycloalkylene group or a heteroarylene group,
to yield the compounds of formula (XI):

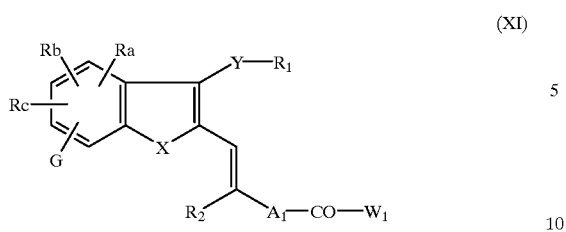
(XI)

wherein Ra, Rb, Rc, G, $R_1$, $R_2$, X, Y, $A_1$ and $W_1$ are as defined hereinbefore, the hydroxy function of which compounds of formula (XI) is deprotected under conventional conditions of organic synthesis, and which are then reacted in a basic medium with a compound of formula (IX):

(IX)

wherein $U_1$, $V_1$, $U_2$ and $V_2$ are as defined for formula (I) and Hal represents a halogen atom, to yield the compounds of formula (I/e), a particular case of the compounds of formula (I):

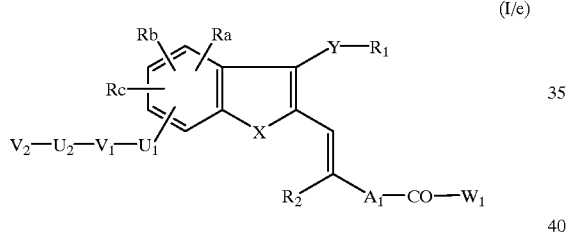
(I/e)

wherein Ra, Rb, Rc, $U_1$, $V_1$, $U_2$, $V_2$, $R_1$, $R_2$, $A_1$, X, Y and $W_1$ are as defined hereinbefore, which compounds of formula (I/e) are, if desired, subjected:
either to conditions of hydrolysis, under basic conditions, to yield the compounds of formula (I/f), a particular case of the compounds of formula (I):

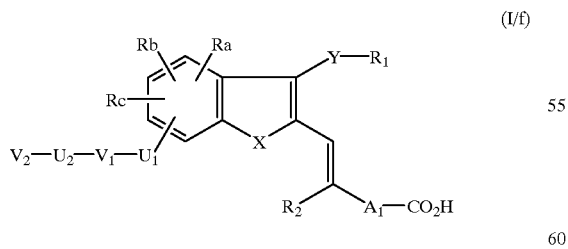
(I/f)

wherein Ra, Rb, Rc, $U_1$, $V_1$, $U_2$, $V_2$, $R_1$, $R_2$, X, Y and $A_1$ are as defined hereinbefore, or to conditions of catalytic hydrogenation to yield the compounds of formula (I/g), a particular case of the compounds of formula (I):

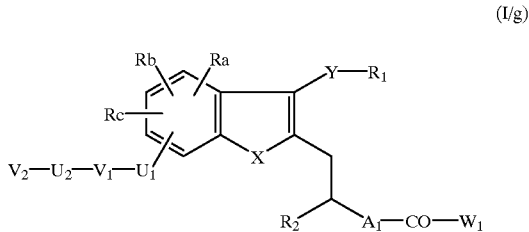
(I/g)

wherein Ra, Rb, Rc, $U_1$, $V_1$, $U_2$, $V_2$, $R_1$, $R_2$, X, Y, $A_1$ and $W_1$ are as defined hereinbefore, which compounds of formula (I/g) may be treated under conditions of basic hydrolysis to yield the compounds of formula (I/h), a particular case of the compounds of formula (I):

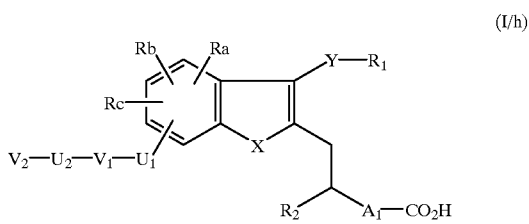
(I/h)

wherein Ra, Rb, Rc, $U_1$, $V_1$, $U_2$, $V_2$, $R_1$, $R_2$, X, Y and $A_1$ are as defined hereinbefore, or the hydroxy function of which compounds of formula (IV) is deprotected under conventional conditions of organic synthesis, and which are then reacted in a basic medium with a compound of formula (IX):

(IX)

wherein $U_1$, $V_1$, $U_2$ and $V_2$ are as defined for formula (I) and Hal represents a halogen atom, to yield the compounds of formula (XII):

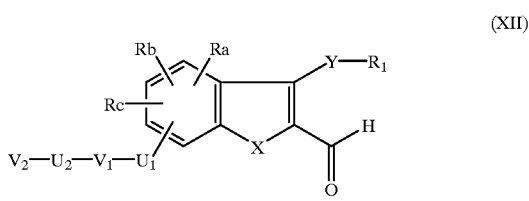
(XII)

wherein Ra, Rb, Rc, $U_1$, $V_1$, $U_2$, $V_2$, $R_1$, X and Y are as defined hereinbefore, the aldehyde function of which compounds of formula (XII) is reduced to the primary alcohol to yield the compounds of formula (XIII):

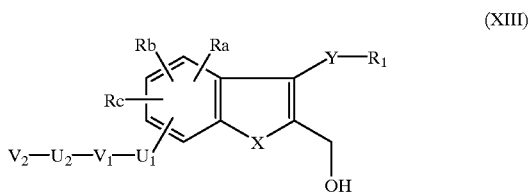
(XIII)

wherein Ra, Rb, Rc, $U_1$, $V_1$, $U_2$, $V_2$, $R_1$, X and Y are as defined for formula (I), the terminal hydroxy of which compounds of formula (XIII) is replaced by a halogen atom, under conventional conditions, to yield the compounds of formula (XIV):

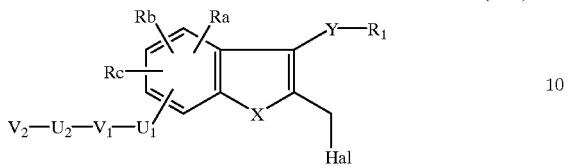

(XIV)

wherein Ra, Rb, Rc, $U_1$, $V_1$, $U_2$, $V_2$, $R_1$, X and Y are as defined hereinbefore and Hal represents a chlorine or bromine atom, in which compounds of formula (XIV):
the halogen atom is replaced, under basic conditions, by an aminated compound of formula (XV):

(XV)

wherein $R_2$ is as defined for formula (I) and $A_1$ and $W_1$ are as defined hereinbefore, to yield the compounds of formula (I/i), a particular case of the compounds of formula (I):

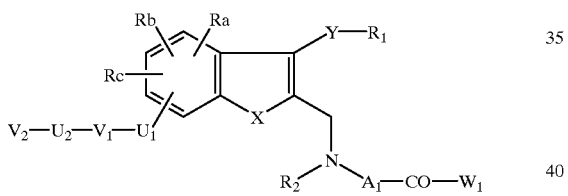

(I/i)

wherein Ra, Rb, Rc, $U_1$, $V_1$, $U_2$, $V_2$, $R_1$, $R_2$, X, Y, $A_1$ and $W_1$ are as defined hereinbefore, the terminal carbonyl group of which compounds of formula (I/i) is hydrolysed under basic conditions to yield the compounds of formula (I/j), a particular case of the compounds of formula (I):

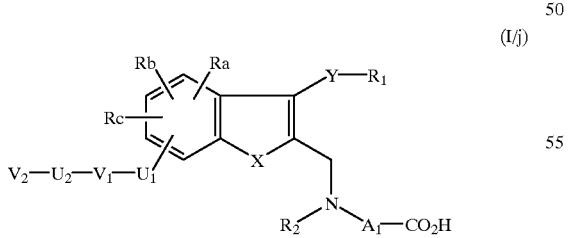

(I/j)

wherein Ra, Rb, Rc, $U_1$, $V_1$, $U_2$, $V_2$, $R_1$, $R_2$, X, Y and $A_1$ are as defined hereinbefore, or which compounds of formula (XIV) are initially treated with sodium azide, the resulting azide being reduced to the primary amine under conditions of catalytic hydrogenation to yield the compounds of formula (XVI):

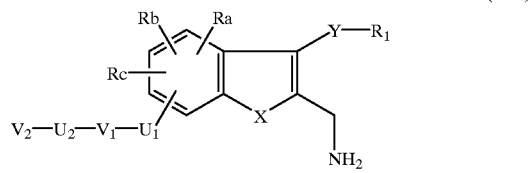

(XVI)

wherein Ra, Rb, Rc, $U_1$, $V_1$, $U_2$, $V_2$, $R_1$, X and Y are as defined for formula (I), which compounds of formula (XV) are condensed, under basic conditions, with a chlorosulphonyl compound of formula (XVII):

Cl—$SO_2$—$R_4$—CO—$W_1$ (XVII)

wherein $R_4$ is as defined for formula (I) and $W_1$ is as defined hereinbefore, to yield the compounds of formula (I/k), a particular case of the compounds of formula (I),

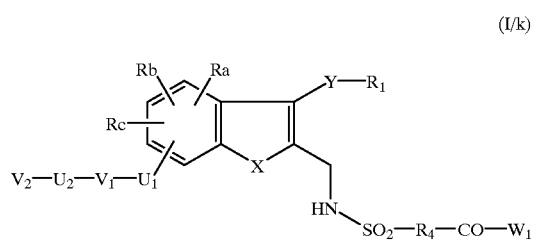

(I/k)

wherein Ra, Rb, Rc, $U_1$, $V_1$, $U_2$, $V_2$, $R_1$, $R_4$, X, Y and $W_1$ are as defined hereinbefore, which compounds of formula (I/k):
are subjected, if desired, to conditions of hydrolysis under basic conditions to yield the compounds of formula (I/l), a particular case of the compounds of formula (I):

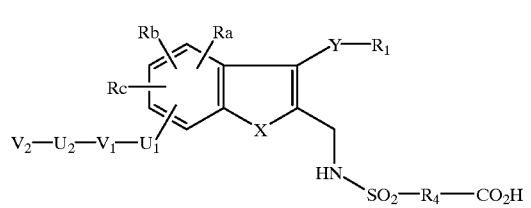

(I/l)

wherein Ra, Rb, Rc, $U_1$, $V_1$, $U_2$, $V_2$, $R_1$, $R_4$, X and Y are as defined hereinbefore, or condensed, in a basic medium, with a compound of formula (XVIII):

Hal—$R'_2$ (XVIII)

wherein Hal represents a halogen atom, such as iodine, and $R'_2$ is as defined hereinbefore, to yield the compounds of formula (I/m), a particular case of the compounds of formula (I):

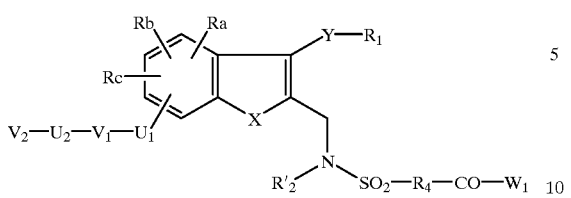

(I/m)

wherein Ra, Rb, Rc, $U_1$, $V_1$, $U_2$, $V_2$, $R_1$, $R'_2$, $R_4$, X, Y and $W_1$ are as defined hereinbefore, which compounds of formula (I/m) are treated under conditions of hydrolysis in a basic medium to yield the compounds of formula (I/n), a particular case of the compounds of formula (I):

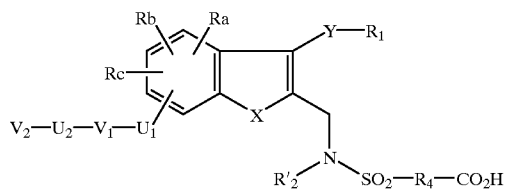

(I/n)

wherein Ra, Rb, Rc, $U_1$, $V_1$, $U_2$, $V_2$, $R_1$, $R'_2$, $R_4$, X and Y are as defined hereinbefore, the totality of the compounds of formulae (I/c), (I/d), (I/f), (I/h), (I/j), (I/l) and (I/n) constituting the compounds of formula (I'):

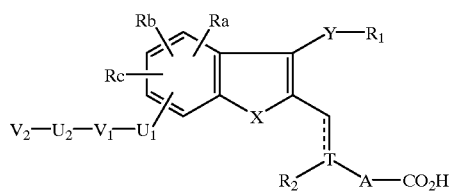

(I')

wherein Ra, Rb, Rc, $U_1$, $V_1$, $U_2$, $V_2$, $R_1$, $R_2$, X, Y, Z and A are as defined for formula (I), which compounds of formula (I') are reacted with an O-substituted hydroxylamine to yield, after deprotection of the hydroxylamine function, the compounds of formula (I/o), a particular case of the compounds of formula (I):

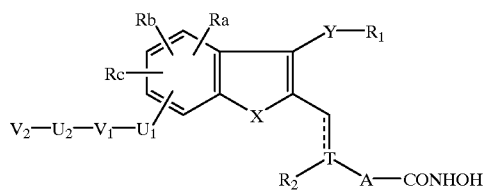

(I/o)

wherein Ra, Rb, Rc, $U_1$, $V_1$, $U_2$, $V_2$, $R_1$, $R_2$, X, Y, Z and A are as defined hereinbefore, the compounds (I/a) to (I/o) constituting the totality of the compounds of the invention, which are purified, if necessary, according to a conventional purification technique, which may be separated, if desired, into their different isomers according to a conventional separation technique, and which are converted, where appropriate, into addition salts thereof with a pharmaceutically acceptable acid or base.

The compounds of formula (II) are obtained according to conventional methods of organic synthesis. In particular, the compounds of formula (II) wherein X represents an oxygen atom and Q represents a hydroxy group, are obtained starting from compounds of formula (II/A):

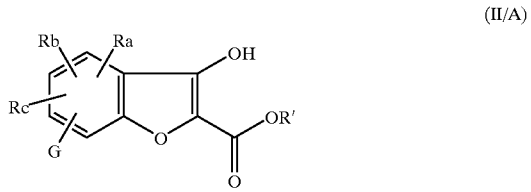

(II/A)

the synthesis scheme of which is described in *J Med Chem.*, 1992, 35, 958–965, and wherein Ra, Rb, Rc and G are as defined hereinbefore and R' represents a linear or branched $(C_1-C_6)$alkyl group, the hydroxy function of which is protected, under basic conditions, by a trialkylsilyl group, and the ester function of which is then reduced, by the action of $LiAlH_4$ for example, to the primary alcohol function, the latter then being oxidised to the aldehyde function, the alcohol function thereof then being deprotected under the action of $n-Bu_4NF$, enabling the particular compounds of formula (II) wherein X represents an oxygen atom and Q represents a hydroxy group to be obtained.

The particular compounds of formula (II) wherein X represents an $NR_3$ group are obtained is starting from compounds of formula (II/B):

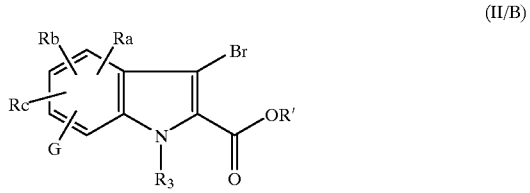

(II/B)

the synthesis scheme of which is described in *Heterocycles*, 1992, 34 (12), 2349–62 and in *Synthesis*, 1984, 862–865, and wherein Ra, Rb, Rc, G and $R_3$ are as defined hereinbefore and R' represents a linear or branched $(C_1-C_6)$alkyl group, the ester function of which is reduced to the primary alcohol function, the latter then being oxidised under the action of manganese dioxide to the aldehyde function to yield the compounds of formula (II) wherein X represents an $NR_3$ group and Q represents a halogen atom.

The particular compounds of formula (II) wherein X represents a sulphur atom are obtained starting from compounds of formula (II/C):

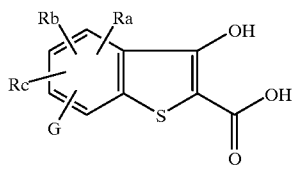

(II/C)

the synthesis scheme of which is described in *J Heterocyclic. Chem.*, 1971, 8 711–714, and wherein Ra, Rb, Rc and G are as defined hereinbefore, the carboxylic acid function of which is first reduced to the primary alcohol and then oxidised to the aldehyde to yield the compounds of formula (II) wherein X represents a sulphur atom and Q represents a halogen atom.

The compounds of formulae (III), (V), (VI), (VII), (IX), (X), (XV), (XVII) and (XVIII) are either commercial products or are obtained according to conventional methods of organic synthesis.

The present invention relates also to pharmaceutical compositions comprising as active ingredient at least one compound of formula (I), its optical isomers or an addition salt thereof with a pharmaceutically acceptable base or acid, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or sub-cutaneous), per- or trans-cutaneous, nasal, rectal, perlingual, ocular or respiratory administration, and especially tablets or dragées, sublingual tablets, sachets, gelatin capsules, lozenges, suppositories, creams, ointments, dermal gels, injectable or drinkable preparations, aerosols, eye or nose drops etc..

The useful dosage varies according to the age and weight of the patient, the route of administration, the nature and severity of the disorder and any associated treatments taken, and ranges from 0.1 mg to 1 g in one or more administrations per day.

The following Examples illustrate the invention but do not limit it in any way.

The starting materials used are known products or are prepared according to known procedures.

The different synthesis steps yield synthesis intermediates that are useful in preparation of the compounds of the invention.

The structures of the compounds described in the Examples and the synthesis steps were determined according to the usual spectrophotometric techniques (infrared, NMR, mass spectrometry etc.).

EXAMPLE 1

Ethyl (E)-3-[5,6-bis-([1,1'-biphenyl]-4-ylmethoxy)3-(4-chlorophenoxy)benzo[b]thiophen-2-yl]-2-(4-pyridyl)2-propenoate Step A: 3-Chloro-5,6-(methylenedioxy)-benzo[b]thiophene-2-carbonyl chloride 0.026 mol of pyridine and, dropwise, 1.33 mol of $SOCl_2$ are added in succession at ambient temperature to a suspension of 0.26 ml of 3,4-(methylenedioxy)cinnamic acid in 365 ml of chlorobenzene. The reaction mixture is then refluxed for 2 days. After returning to ambient temperature, a precipitate forms. After filtration, rinsing with hexane and drying, 51.2 g of the expected product are obtained.

Step B: 3-Chloro-5,6-(methylenedioxy)-benzo[b]thiophene-2-carboxylic acid 40 ml of water are added to a solution of 70 mmol of the compound of Step A in 250 ml of dioxane. After 20 hours' reflux and then return to ambient temperature, a precipitate forms. After filtration and rinsing with water until neutral, the precipitate is dried over $P_2O_5$ under reduced pressure, allowing the expecting product to be isolated.

Step C: (3-Chloro-5,6-(methylenedioxy)-benzo[b]thiophen-2-yl)methanol 0.14 mol of the compound obtained in Step B is added at 5° C. under an inert atmosphere to a solution of 0.15 mol of $LiAlH_4$ in 450 ml of tetrahydrofuran. After 2 hours' reaction at ambient temperature, the reaction mixture is hydrolysed by the addition of 85 ml of isopropanol and 31 ml of saturated sodium chloride solution. After stirring for 12 hours at ambient temperature, the reaction mixture is filtered over Celite. The organic phase is then concentrated under reduced pressure, taken up in dichloromethane and washed with water and then with saturated NaCl solution. After the organic phase has been dried over calcium sulphate, the solution is concentrated under reduced pressure, allowing the expected product to be obtained.

Step D: 3-Chloro-5,6-(methylenedioxy)-benzo[b]thiophene-2-carbaldehyde 3.5 equivalents of $MnO_2$ are added at ambient temperature under an inert atmosphere to a suspension of 0.12 mol of the compound obtained in Step C in 925 ml of anhydrous dioxane. After 3.5 hours' reaction at reflux, the reaction mixture is filtered while hot over Celite and rinsed with dioxane; the filtrate is then concentrated under reduced pressure. The residue obtained is taken up in 100 ml of ethyl acetate and the solution obtained is refluxed and then returned to ambient temperature. A precipitate forms, which is filtered off, rinsed with ethyl acetate and then with water and pentane, and finally dried in vacuo, allowing the expecting product to be isolated.

Step E: 3-(4-Chlorophenoxy)-5,6-(methylenedioxy)benzo[b]thiophene-2-carbaldehyde 1 equivalent of sodium hydride and then 0.094 mol of the product obtained in Step D are added at ambient temperature and under an inert atmosphere to a solution of 0.10 mol of 4-chlorophenol in 250 ml of dimethylformamide. After 12 hours' reaction at 80° C., the reaction mixture is concentrated under reduced pressure. The residue is then diluted with ethyl acetate, washed with water and then with an aqueous solution of NaOH and then of NaCl, dried over calcium sulphate, filtered and concentrated under reduced pressure. Chromatography over silica gel (dichloromethane/ethyl acetate: 98/2) allows the expected product to be isolated.

Step F: Ethyl (E)-3-[3-(4-Chlorophenoxy)-5,6-(methylenedioxy)benzo[b]thiophen-2-yl]-2-(4-pyridyl)-2-propenoate A solution containing 85 mmol of the product obtained in Step E, 127 mmol of ethyl 4-pyridylacetate and 75 ml of acetic anhydride is heated at 100° C. for 18 hours. After returning to ambient temperature, the reaction mixture is hydrolysed by saturated $NaHCO_3$ solution and extracted with ethyl acetate. The organic phases are then washed with water and then with NaCl solution, dried over calcium sulphate, filtered and concentrated under reduced pressure. Chromatography over silica gel (dichloromethane/ethanol : 98/2) allows the expected product to be isolated.

Step G: Ethyl (E)-3-[3-(4-chlorophenoxy)-5,6-(dihydroxy)-benzo[b]thiophen-2-yl]-2-(4-pyridyl)-2-propenoate 0.1 mol of $BBr_3$, as a 1M solution in dichloromethane, is added dropwise at 5° C. and under argon to a solution of 0.025 mol of the product obtained in Step F in 170 ml of anhydrous dichloromethane. After stirring for 2 hours, 125 ml of alcohol are added dropwise to the reaction mixture, which is then concentrated under reduced pressure. The residue is taken up in ethyl acetate and stirred for 30 minutes. The precipitate formed is filtered off, rinsed with ethyl acetate and then dried in vacuo, allowing the expected product to be isolated.

Step H: Ethyl (E)-3-[5,6-bis-([1,1'-biphenyl]-4-ylmethoxy)-3-(4-chlorophenoxy)-benzo[b]thiophen-2-yl]-2-(4pyridyl)-2-propeneate 7.5 mmol of $K_2CO_3$ are added to a solution of 2.1 mmol of the product obtained in Step G and 4.6 mmol of 4-(chloromethyl)-1,1'-biphenyl in 30 ml of anhydrous dimethylformamide. After 12 hours at 80° C., the reaction mixture is returned to ambient temperature and 30 ml of water are added, causing the formation of a precipitate. The precipitate is filtered off, rinsed with water and then dried in vacuo. Chromatography over silica gel (dichloromethane/ethyl acetate: 95/5) allows the expected product to be isolated.

Melting point: 212° C.

Elemental microanalysis:

|  | % C | % H | % S | % Cl | % N |
|---|---|---|---|---|---|
| calculated | 75.03 | 4.79 | 4.01 | 4.43 | 1.75 |
| found | 75.34 | 4.97 | 3.62 | 4.69 | 1.81 |

EXAMPLE 2

(E)-3-[5,6-Bis-([1,1'-biphenyl]-4-ylmethoxy)-3-(4-chlorophenoxy)-benzo[b]thiophen-2-yl]-2-(4-pyridyl)2-propenoic acid A solution containing 1.5 mmol of the product of Example 1, 3 ml of an aqueous 1N sodium hydroxide solution and 30 ml of ethanol is refluxed for 12 hours. After returning to ambient temperature, the reaction mixture is concentrated under reduced pressure and the residue is then diluted with water and subsequently taken up in ethyl ether. The organic phase is then acidified by the addition of 6 ml of 1N HCl solution. A precipitate forms, which is filtered off, rinsed with water and then dried under reduced pressure, allowing the expected compound to be obtained.

Elemental microanalysis:

|  | % C | % H | % Cl | % N | % S |
|---|---|---|---|---|---|
| calculated | 74.65 | 4.44 | 4.59 | 1.81 | 4.15 |
| found | 74.69 | 4.46 | 4.50 | 1.90 | 4.04 |

EXAMPLE 3

Sodium (E)-3-[5,6-bis-([1,1'-biphenyl]-4-ylmethoxy)3-(4-chlorophenoxy)benzo[b]thiophen-2-yl]-2-(4pyridyl2-propenoate Water is added to a suspension of 1 g of the product of Example 2 in 2.5 ml of 1N sodium hydroxide solution until completely diluted. Lyophilisation allows the expected product to be isolated.

EXAMPLE 4

(E)-3-[5,6-Bis-([1,1'-biphenyl]-4-ylmethoxy)-3-(4-chlorophenoxy)-benzo[b]thiophen-2-yl]-2-phenyl-2-propenoic acid The procedure is as in Example 1. Steps A to H, using phenylethanoic acid as reagent in Step F.

EXAMPLE 5

Ethyl (E)-3-[5,6-bis-([1,1'-biphenyl]-4-ylmethoxy)-3-(4-chlorophenoxy)-benzo[b]thiophen-2-yl]-propenoate 20 ml of a 1M solution of potassium tert-butylate in tetrahydrofuran are added dropwise at 0° C. under an inert atmosphere to a suspension of 0.02 mol of (ethoxycarbonylmethyl)triphenylphosphonium bromide in 90 ml of tetrahydrofuran. After the addition is complete and the mixture has returned to ambient temperature, 0.01 mol of the compound obtained in Step E of Example 1 diluted with 30 ml of tetrahydrofuran is added. After 12 hours, the reaction mixture is hydrolysed by the addition of 100 ml of 1N HCl solution and is then extracted with ethyl acetate; the combined organic phases are washed with water and then with saturated NaCl solution, dried over sodium sulphate, filtered and concentrated under reduced pressure. Chromatography over silica gel (pentane/ethyl acetate : 90/10) allows the expected product to be isolated.

EXAMPLE 6

Ethyl 2-({[5,6-bis-([1,1'-biphenyl]-4-ylmethoxy)-3-(4-chlorophenoxy)-benzo[b]thiophen-2-yl]methyl}anilino)acetate Step 1: [5,6-(Methylenedioxy)-3-(4-chlorophenoxy)-benzo[b]thiophen-2-yl]methanol 26 mmol of $NaBH_4$ are added at ambient temperature to a solution of 24 mmol of the compound obtained in Step E of Example 1 in 100 ml of methanol. After reacting for 2 hours, one equivalent of $NaBH_4$ is added to the reaction mixture. After reacting for 12 hours, the solution is concentrated and then diluted with ethyl acetate, washed with 1N HCl solution, then with water and then with saturated NaCl solution, subsequently dried over calcium sulphate, filtered and concentrated under reduced pressure. Chromatography over silica gel (dichloromethane/ethyl acetate: 95/5) allows the expected product to be isolated.

Step 2: [2-Chloromethyl-3-(4-chlorophenoxy)-5,6-(methylenedioxy)]-benzo[b]thiophene 0.63 ml of $SOCl_2$ is added dropwise at 0° C. to 4 mmol of the compound of Step 1 diluted with 10 ml of dichloromethane. After returning to ambient temperature, followed by heating at reflux of the dichloromethane for 6 hours, the reaction mixture is concentrated under reduced pressure, allowing the expected product to be obtained.

Step 3: Ethyl 2-({[3-(4-chlorophenoxy)-5,6-(methylenedioxy)benzo[b]thiophen-2-yl]-methyl}anilino)acetate A solution containing 6.5 mmol of the compound obtained in Step 2, in 16 ml of dimethylformamide, 1.5 equivalents of N-phenylglycine ethyl ester and 1.5 equivalents of $K_2CO_3$ is heated at 80° C. for 18 hours. After evaporating off the solvent, the residue is diluted with ethyl acetate and the organic phase is washed with water and then with saturated NaCl solution, dried over calcium sulphate, filtered and evaporated under reduced pressure. Chromatography over silica gel (toluene/ethyl acetate: 98/2) allows 2.56 g of the expected product to be isolated in the form of an oil.

Step 4: Ethyl 2-({[5,6-bis-([1,1'-biphenyl]-4-ylmethoxy)-3-(4-chlorophenoxy)benzo[b]thiophen-2-yl]methyl}anilino)acetate The procedure is as in Example 1, Steps G to H, using the product obtained in Step 3 above as substrate.

EXAMPLE 7

Ethyl 2-({[5,6-bis-([1,1'-biphenyl]-4-ylmethoxy)-3-(4-chlorophenoxy)-benzo[b]thiophen-2-yl]methyl}amino)benzoate The procedure is as in Example 6, using ethyl anthranilate as reagent in Step 3.

EXAMPLE 8

Methyl 2-[({[5,6-bis-([1,1'-biphenyl]-4-ylmethoxy)
3-(4-chlorophenoxy)-benzo[b]thiophen-2-yl]
methyl}amino)sulphonyl]benzoate Step 1: [2-Azidometyl-3-(4-chlorophenoxy)-5,6-(methylenedioxy)]-benzo[b]thiophene A solution containing 41 mmol of the compound obtained in Step 2 of Example 6 and 78 mmol of sodium azide in 80 ml of dimethylformamide is stirred at ambient temperature for 48 hours. The reaction medium is then concentrated under reduced pressure. The residue is diluted with ethyl acetate and washed with water and then with saturated NaCl solution. The organic phase is then dried over calcium sulphate, filtered and evaporated, allowing the expected product to be obtained.

Step 2: [2-Aminomethyl-3-(4-chlorophenoxy)-5,6-(methylenedioxy)]-benzo[b]thiophene A solution containing 41 mmol of the compound obtained in Step 1 above and 1 g of Pd/C in 6.5 ml of chloroform and 300 ml of anhydrous methanol is placed under a hydrogen atmosphere at ambient temperature. After 12 hours, the reaction mixture is filtered and concentrated under reduced pressure, allowing the expected product to be obtained.

Step 3: Methyl 2-[({[-3-(4-chlorophenoxy)-5,6-(methylenedioxy)-benzo[b]thiophen-2-yl]-methyl}amino)sulphonyl]benzoate A solution containing 6.5 mmol of the compound obtained in Step 2 above, 6.5 mmol of methyl 2-(chlorosulphonyl)benzoate and 15.7 mmol of N-methylmorpholine in 50 ml of dichloromethane is stirred at ambient temperature. After 12 hours, the reaction mixture is washed with water and then with saturated NaCl solution, dried over sodium sulphate and concentrated under reduced pressure. Chromatography over silica gel (dichloromethane/ethyl acetate : 98/2) allows the expected product to be isolated.

Step 4: Methyl 2-[({[5,6-bis-([1,1'-biphenyl]-4-ylmethoxy)-3-(4-chlorophenoxy)benzo[b]thiophen-2-yl]methyl}amino)sulphonyl]benzoate The procedure is as in Example 1, Steps G to H, using the product obtained in Step 3 above as substrate.

EXAMPLE 9

2-[({[5,6-Bis-([1,1'-biphenyl]-4-ylmethoxy)-3-(4-chlorophenoxy)-benzo[b]thiophen-2-yl]
methyl}amino)sulphonyl]benzoic acid The procedure is as in Example 2, using the compound obtained in Step 4 of Example 8 as substrate.

EXAMPLE 10

(E)-3-[5,6-Bis([1,1'-biphenyl]-4-ylmethoxy)-3-(3-pyridyloxy)-benzo[b]thiophen-2-yl]-2-4-pyridyl)-2-propenoic acid The procedure is as in Example 1, using 3-hydroxypyridine as reagent in Step E, and then following the protocol described in Example 2.

Melting point: 237° C.

Elemental microanalysis:

|  | % C | % H | % N | % S |
|---|---|---|---|---|
| calculated | 76.40 | 4.64 | 3.79 | 4.34 |
| found | 76.69 | 4.63 | 3.83 | 4.28 |

EXAMPLE 11

(E)-3-[5,6-Bis-([1,1'-biphenyl]-4-ylmethoxy)-3-(4-chlorophenoxy)-1H-2-indolyl]-2-(4-pyridyl)-2-propenoic acid The procedure is as in Example 1, from Step E to Step H, using 3-bromo-5,6-dimethoxy-1H-2-indolecarbaldehyde as substrate in Step E, and then following the protocol described in Example 2.

EXAMPLE 12

(E)-3-[5,6-Bis-([1,1'-biphenyl]-4-ylmethoxy)-3-[(4-methoxyphenylsuphanyl]benzo[b]thiophen-2-yl]-2-(4pyridyl)-2-propenoic acid The procedure is as in Example 1, using 4-methoxybenzenethiol as reagent in Step E, and then following the protocol described in Example 2.

EXAMPLE 13

3-(E)-{3-[4-(2-(Dimethylamino)ethoxy)-phenoxy]-5,6-bis-([1,1'-biphenyl]-4-ylmethoxy)-benzo[b]
thiophen-2-yl}-2-phenyl-2-propenoic acid The procedure is as in Example 1, using 2-(dimethylamino)ethoxyphenol as reagent in Step E and phenylethanoic acid as reagent in Step F, and then following the protocol described in Example 2.

EXAMPLE 14

(E)-3-[5,6-Bis-([1,1'-biphenyl]-4-ylmethoxy)-3-(3,4-dichlorophenoxy)-benzo[b]thiophen-2-yl]-2-(4pyridyl)2-propenoic acid The procedure is as in Example 1, using 3,4-dichlorophenol as reagent in Step E, and then following the protocol described in Example 2.

EXAMPLE 15

3-(E)-{5,6-Bis-([1,1'-biphenyl]-4-ylmethoxy)-3-[(6-(methyl)pyridyl-3-oxy]-benzo[b]thiophen-2-yl}-2-(4-pyridyl)-2-propenoic acid The procedure is as in Example 1, using 2-methyl-5-hydroxypyridine as reagent in Step E, and then following the protocol described in Example 2.

Elemental microanalysis:

|  | % C | % H | % N | % S |
|---|---|---|---|---|
| calculated | 76.58 | 4.82 | 3.72 | 4.26 |
| found | 76.84 | 4.72 | 3.77 | 4.15 |

EXAMPLE 16

3-(E)-[5,6-Bis-([1,1'-biphenyl]-4-ylmethoxy)-3-(6-quinolyloxy)-benzo[b]thiophen-2-yl]-2-(4-pyridyl)-2-propenoic acid The procedure is as in Example 1, using 6-hydroxyquinoline as reagent in Step E, and then following the protocol described in Example 2.

Elemental microanalysis:

|  | % C | % H | % N | % S |
|---|---|---|---|---|
| calculated | 77.65 | 4.60 | 3.55 | 4.06 |
| found | 78.00 | 4.75 | 3.59 | 3.71 |

EXAMPLE 17

(E)-3-[5,6-Bis-([1,1'-biphenyl]-2-ylmethoxy)-3-(4chlorophenoxy)-benzo[b]thiophen-2-yl]-2-(4-pyridyl)-2-propenoic acid The procedure is as in Example 1, using 2-(bromomethyl)-1,1'-biphenyl as reagent in Step H, and then following the protocol described in Example 2.

Elemental microanalysis:

|  | % C | % H | % N | % S | % Cl |
|---|---|---|---|---|---|
| calculated | 74.65 | 4.44 | 1.81 | 4.15 | 4.59 |
| found | 74.97 | 4.55 | 1.88 | 4.06 | 4.57 |

EXAMPLE 18

(E)-3-[5,6-Bis-(4-phenoxyphenoxy)-3-(4-chlorophenoxy)-benzo[b]thiophen-2-yl]-2-(4-pyridyl)-2-propenoic acid The procedure is as in Example 1, using 1-bromo-4-phenoxybenzene as reagent in Step H, and then following the protocol described in Example 2.

EXAMPLE 19

(E)-3-{3-(4-Chlorophenoxy)-5,6-bis-[4-(4-pyridylmethyl)phenoxy]-benzo[b]thiophen-2-yl}-2-(4-pyridyl)-2-propenoic acid The procedure is as in Example 1, using 4-(4-chlorobenzyl)pyridine as reagent in Step H, and then following the protocol described in Example 2.

EXAMPLE 20

(E)-3-[5,6-Bis([1,1'-biphenyl]-3-ylmethoxy)-3-(4-chlorophenoxy)-benzo[b]thiophen-2-yl]-2-(4-pyridyl)2-propenoic acid The procedure is as in Example 1, using 3-(bromomethyl)-1,1'-biphenyl as reagent in Step H, and then following the procedure described in Example 2.

Melting point: 205–210° C.

EXAMPLE 21

(E)-3-[5,6-Bis([1,1'-biphenyl]-4-ylmethoxy)-3-(4-chloro-3-fluorophenoxy)-benzo[b]thiophen-2-yl]-2-(4-pyridyl)-2-propenoic acid The procedure is as in Example 1, using 4-chloro-3-fluorophenol as reagent in Step E, and then following the protocol described in Example 2.

Elemental microanalysis:

|  | % C | % H | % N | % S |
|---|---|---|---|---|
| calculated | 72.95 | 4.21 | 1.77 | 4.06 |
| found | 72.85 | 4.27 | 1.79 | 3.65 |

EXAMPLE 22

(E)-3-[5,6-Bis([1,1'-biphenyl]-4-ylmethoxy)-3-(4-chloro-3,5dimethylphenoxy)-benzo[b]thiophen-2-yl]-2-(4-pyridyl)2-propenoic acid The procedure is as in Example 1, using 4-chloro-3,5-dimethylphenol as reagent in Step E, and then following the protocol described in Example 2.

Elemental microanalysis:

|  | % C | % H | % N | % S | % Cl |
|---|---|---|---|---|---|
| calculated | 75.03 | 4.79 | 1.75 | 4.01 | 4.43 |
| found | 74.45 | 4.91 | 1.80 | 3.51 | 4.19 |

EXAMPLE 23

(E)-3-[5,6-Bis([1,1'-biphenyl]-4-ylmethoxy)-3-(4-chloro-3-methylphenoxy)-benzo[b]thiophen-2-yl]-2-(4-pyridyl)-2-propenoic acid The procedure is as in Example 1, using 4-chloro-3-methylphenol as reagent in Step E, and then following the protocol described in Example 2.

Elemental microanalysis:

|  | % C | % H | % N | % S | % Cl |
|---|---|---|---|---|---|
| calculated | 74.85 | 4.61 | 1.78 | 4.08 | 4.51 |
| found | 74.64 | 4.77 | 1.83 | 4.00 | 4.39 |

EXAMPLE 24

(E)-3-{5,6-Bis([1,1'-biphenyl]-4-ylmethoxy)-3-[4-(4-pyridyloxy)phenoxy]-benzo[b]thiophen-2-yl}-2-(4-pyridyl)-2-propenoic acid The procedure is as in Example 1, using 4-pyridyloxyphenol as reagent in Step E, and then following the protocol described in Example 2.

Melting point: 265° C.

Elemental microanalysis:

|  | % C | % H | % N | % S |
|---|---|---|---|---|
| calculated | 76.61 | 4.61 | 3.37 | 3.86 |
| found | 76.66 | 4.72 | 3.40 | 3.46 |

EXAMPLE 25

(E)-3-{5,6-Bis([1,1'-biphenyl]-4-ylmetboxy)-3-[4-(1H-imidazol-1-yl)-phenoxy]-benzo[b]thiophen-2-yl}-2-(4pyridyl)-2-propenoic acid The procedure is as in Example 1, using 4-(1H-imidazol-1-yl)-phenol as reagent in Step E, and then following the protocol described in Example 2.

Elemental microanalysis:

|  | % C | % H | % N | % S |
|---|---|---|---|---|
| calculated | 76.20 | 4.64 | 5.23 | 3.99 |
| found | 75.97 | 4.68 | 5.17 | 3.92 |

EXAMPLE 26

(E)-3-[5,6-Bis([1,1'-biphenyl]-4-ylmethoxy)-3-phenoxy-benzo[b]thiophen-2-yl]-2-(4-pyridyl)-2-propenoic acid The procedure is as in Example 1, using phenol as reagent in Step E, and then following the protocol described in Example 2.

Elemental microanalysis:

|  | % C | % H | % N | % S |
|---|---|---|---|---|
| calculated | 78.13 | 4.78 | 1.90 | 4.35 |
| found | 78.30 | 4.88 | 1.94 | 4.16 |

EXAMPLE 27

(E)-3-[5,6-Bis([1,1'-biphenyl]-4-ylmethoxy)-3-(3-fluorophenoxy)-benzo[b]thiophen-2-yl]-2-(4-pyridyl)-2-propenoic acid The procedure is as in Example 1, using 3-fluorophenol as reagent in Step E, and then following the protocol described in Example 2.

Elemental microanalysis:

|  | % C | % H | % N | % S |
|---|---|---|---|---|
| calculated | 76.27 | 4.53 | 1.85 | 4.24 |
| found | 76.37 | 4.56 | 1.90 | 4.05 |

EXAMPLE 28

(E)-3-[5,6-Bis([1,1'-biphenyl]-4-ylmethoxy)-3-(3,4-difluorophenoxy)benzo[b]thiophen-2-yl]-2-(4-pyridyl)-2-propenoic acid The procedure is as in Example 1, using 3,4-difluorophenol as reagent in Step E, and then following the protocol described in Example 2.

Elemental microanalysis:

|  | % C | % H | % N | % S |
|---|---|---|---|---|
| calculated | 74.50 | 4.30 | 1.81 | 4.14 |
| found | 74.48 | 4.24 | 1.88 | 3.98 |

EXAMPLE 29

(E)-3-{5,6-Bis([1,1'-biphenyl]-4-ylmethoxy)-3-[(6-chloro-3-pyridyl)oxy]-benzo[b]thiophen-2-yl}-2-(4-pyridyl)-2-propenoic acid The procedure is as in Example 1, using 2-chloro-5-hydroxypyridine as reagent in Step E, an then following the protocol described in Example 2.

Elemental microanalysis:

|  | % C | % H | % N | % S | % Cl |
|---|---|---|---|---|---|
| calculated | 70.98 | 4.06 | 3.52 | 4.03 | 4.46 |
| found | 71.27 | 4.44 | 3.53 | 3.51 | 4.30 |

EXAMPLE 30

(E)-3-{3-(4-Chlorophenoxy)-5,6-bis[(4'-methoxyl[1,1'-biphenyl]-4-yl)methoxy]-benzo[b]thiophen-2-yl}-2-(4-pyridyl)2-propenoic acid The procedure is as in Example 1, using 4-(bromomethyl)-4'-methoxy-1,1'-biphenyl as reagent Step H, and then following the procedure described in Example 2.

Melting point: 235° C.

Elemental microanalysis:

|  | % C | % H | % N | % S | % Cl |
|---|---|---|---|---|---|
| calculated | 72.15 | 4.60 | 1.68 | 3.85 | 4.26 |
| found | 71.97 | 4.55 | 1.82 | 4.03 | 4.33 |

EXAMPLE 31

(E)-3-[5,6-Bis(2-[1,1'-biphenyl]-4-ylethoxy)-3-(4-chlorophenoxy)benzo[b]thiophen-2-yl]-2-(4-pyridyl)2-propenoic acid The procedure is as in Example 1, using 4-(2-bromoethyl)-1,1'-biphenyl as reagent in Step H, an then following the procedure described in Example 2.

EXAMPLE 32

(E)-3-[5,6-Bis[(4-benzylbenzyl)oxy]-3-(4-chlorophenoxy)-benzo[b]thiophen-2-yl]-2-(4-pyridyl)-2-propenoic acid The procedure is as in Example 1, using 1-benzyl-4-(bromomethyl)benzene as reagent in Step H, and then following the procedure described in Example 2.

EXAMPLE 33

(E)-3-{3-(4-Chlorophenoxy)-5,6-bis[(4-phenoxybenzyl)oxy]-benzo[b]thiophen-2-yl}-2-(4-pyridyl)-2-propenoic acid The procedure is as in Example 1, using 1-(bromomethyl)-4-phenoxybenzene as reagent in Step H, and then following the procedure described in Example 2.

EXAMPLE 34

(E)-3-(3-(4-Chlorophenoxy)-5,6-bis{[4-(phenylsulphanyl)benzyl]oxy}benzo[b]thiophen-2-yl)-2-(4-pyridyl)2-propenoic acid The procedure is as in Example 1, using 1-(bromomethyl)-4-(phenylsulphanyl)benzene as reagent in Step H, and then following the procedure described in Example 2.

EXAMPLE 35

(E)-3-(3-(4-Chlorophenoxy5,6-bis{[4-(phenylsulphonyl)benzyl]oxy}benzo[b]thiophen-2-yl)2-(4-pyridyl)2-propenoic acid The procedure is as in Example 1, using 1-(bromomethyl)-4-(phenylsulphonyl)benzene as reagent in Step H, and then following the procedure described in Example 2.

EXAMPLE 36

(E)-3-[3-(4-Chlorophenoxy)-5,6-bis({4-[(4-phenoxyphenyl)sulphonyl]benzyl}oxy)-benzo[b]thiophen-2-yl]-2-4-pyridyl)-2-propenoic acid The procedure is as in Example 1, using 1-(bromomethyl)-4-[(4-phenoxyphenyl)sulphonyl]benzene as reagent in Step H, and then following the procedure described in Example 2.

EXAMPLE 37

(E)-3-[6-(Benzyloxy)5-([1,1'-biphenyl]-4-ylmethoxy)-3-(4-chlorophenyl)-benzo[b]thiophen-2-yl]-2-(4-pyridyl)-2-propenoic acid Step 1: (E)-3-[6-(Benzyloxy)-3-(4-chlorophenoxy)-5-hydroxy-benzo[b]thiophen-2-yl]-2-(4-pyridyl)-2-propenoic acid The procedure is as in Example 1, Steps A to H, using chloromethylphenyl.

Step 2: (E)-3-[6-(Benzyloxy)-5-([1,1'-biphenyl]-4-ylmethoxy)-3-(4-chlorophenoxy)-benzo[b]thiophen-2-yl]-2-(4-pyridyl)-2-propenoic acid The procedure is as in Step H of Example 1, and then following the procedure described in Example 2.

Elemental microanalysis:

|  | % C | % H | % N | % S | % Cl |
|---|---|---|---|---|---|
| calculated | 72.46 | 4.34 | 2.01 | 4.61 | 5.09 |
| found | 73.39 | 4.38 | 2.14 | 4.34 | 5.08 |

EXAMPLE 38

(E)-3-[6-([1,1'-Biphenyl]-4-ylmethoxy)-3-(4-chlorophenoxy)-5-phenoxy-benzo[b]thiophen-2-yl]-2-(4pyridyl)-2-propenoic acid The procedure is as in Example 1, using 4-chloromethyl-(1,1'-biphenyl) and then chloromethylphenyl as reagents in Step H.

EXAMPLE 39

3-[6-([1,1'-Biphenyl]-4ylmethoxy)-5-[(1,1'-biphenyl]-4-yloxy)-3-(4-chlorophenoxy)-benzo[b]thiophen-2-yl]-2-phenylpropanoic acid The procedure is as in Example 1, Steps A to F, using phenylethanoic acid instead of the ethyl 4-pyridylacetate as reagent in Step F, and then Steps G to H described in Example 1. The product so obtained is then treated with a current of hydrogen in the presence of 10% Pd/C in methanol for 24 hours. Filtration over Celite at the end of the reaction, followed by chromatography over silica gel, allows the expected product to be isolated.

EXAMPLE 40

2-({[6-([1,1'-Biphenyl]-4-ylmethoxy)-5-([1,1'-biphenyl]-4yloxy)-3-(4-chlorophenoxy)-benzo[b]thiophen-2-yl]methyl}amino)benzoic acid The procedure is as in Example 2, using the compound obtained in Example 7 as starting material.

Pharmacological Study of the Compounds of the Invention

EXAMPLE 41

Inhibition of the Activity of PAI-1

Inhibition of the activity of PAI-1 was effected in vitro in microplate wells in which the formation and then breakdown of a fibrin clot is monitored continuously by measurement of its turbidity using a spectrophotometer. To do so, using, as diluent, a 50 mM phosphate buffer pH 7.4 containing 0.05% of bovine serum albumin, 50 $\mu$m of the inhibitor is placed in the presence of 50 $\mu$l of a 2 nM solution of recombinant active human PAI-1 for 5 minutes at ambient temperature. 50 $\mu$l of a 0.42 nM solution of tissue plasminogen activator, 50 $\mu$l of an 800 nM solution of human plasminogen and 50 $\mu$l of a 2 g/liter solution of fibrinogen are then added and the fibrin formation is triggered by the addition of 50 $\mu$l of 14 nM purified human thrombin. In the absence of the product, inhibition of breakdown two hours after the start of fibrin formation is measured by the absorbance of the clot and represents 100% of the PAI-1 activity. In the absence of the product and of PAI-1, breakdown is measured by the absorbance of the broken-down clot and represents 0% of the PAI-1 activity. The concentration of product that inhibits PAI-1 activity by 50% is determined by measuring the absorbance of the clot two hours after fibrin formation in the presence of PAI-1 and of an increasing concentration of the product. By way of example, the compounds of Examples 2, 10 and 26 have an $IC_{50}$ of 0.13 $\mu$M, 0.53 $\mu$M and 0.06 $\mu$M, respectively. That result demonstrates the very superior fibrinolytic activity of the compounds of the invention, the reference product, XR 5082, having an $IC_{50}$ of 190 $\mu$M.

EXAMPLE 42

Pharmaceutical Composition

Formulation for the preparation of 1000 tablets each containing 10 mg of active ingredient:

| Compound of Example 2 | 10 g |
|---|---|
| Hydroxypropyl cellulose | 2 g |
| Polyvinylpyrrolidone | 2 g |
| Wheat starch | 10 g |
| Lactose | 100 g |
| Magnesium stearate | 3 g |

What is claimed is:
1. A compound selected from those of formula (I):

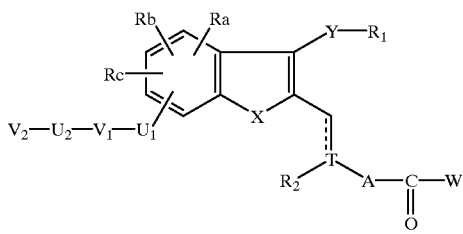

wherein:
- X represents sulphur,
- Y represents oxygen, sulphur, $NR_3$ wherein $R_3$ is hydrogen, linear or branched ($C_1$–$C_6$)alkyl, linear or branched ($C_1$–$C_6$)acyl, aryl, aryl-($C_1$–$C_6$)alkyl in which alkyl is linear or branched or heteroaryl-($C_1$–$C_6$)alkyl in which alkyl is linear or branched,
- T represents nitrogen when bond that links it to adjacent carbon atom is single (—), and, carbon or CH depending on whether the bond that links it to adjacent carbon is single (—) or double (═),
- A represents single bond, or a group selected from ($C_1$–$C_6$)alkylene (optionally substituted by one or more groups selected from linear or branched ($C_1$–$C_6$)alkyl, aryl, aryl-($C_1$–$C_6$)alkyl in which alkyl is linear or branched, cycloalkyl, heterocycloalkyl, and heteroaryl), arylene, cycloalkylene, heterocycloalkylene, heteroarylene, and —$SO_2$—$R_4$— ($SO_2$ being linked to T) wherein $R_4$ represents a group selected from linear or branched ($C_1$–$C_6$)alkylene, arylene, aryl-($C_1$–$C_6$)alkylene in which alkylene is linear or branched, cycloalkylene, heterocycloalkylene, and heteroarylene,
- W represents a group selected from hydroxy, linear or branched ($C_1$–$C_6$)alkoxy, aryloxy, aryl-($C_1$–$C_6$)alkoxy in which alkoxy is linear or branched, cycloalkyloxy, heterocycloalkyloxy, heteroaryloxy, amino (which may itself be substituted by one or two, identical or different, groups each independently of the other selected from linear or branched ($C_1$–$C_6$)alky, aryl, aryl-($C_1$–$C_6$)alkyl in which alkyl is linear or branched, and cycloalkyl), and hydroxyamino,
- $U_1$ represents oxygen, sulphur, or linear or branched ($C_1$–$C_6$)alkylene wherein one or more carbon atoms may optionally be replaced by one or more hetero atoms selected from oxygen, nitrogen, and sulphur, the said alkylene being optionally substituted by one or more, identical or different, groups selected from halogen, hydroxy, linear or branched ($C_1$–$C_6$)alkyl, and linear or branched ($C_1$–$C_6$)alkoxy,
- $V_1$ represents arylene,
- $U_2$ represents a single bond, oxygen, nitrogen, sulphur, linear or branched ($C_1$–$C_6$)alkylene wherein one or more carbon may optionally be replaced by one or more, identical or different, groups selected from oxygen, sulphur, and nitrogen (nitrogen being substituted by a group selected from hydrogen, and linear or branched ($C_1$–$C_6$)alkyl), and $SO_2$,
- $V_2$ represents aryl,
- Ra, Rb, and Rc, which may be identical or different, each independently of the others represents a group selected from:
  hydrogen, halogen,
  hydroxy, cyano, nitro,
  linear or branched ($C_1$–$C_6$)alkyl, linear or branched ($C_1$–$C_6$)alkoxy, linear or branched ($C_1$–$C_6$)acyl, carboxy, linear or branched ($C_1$–$C_6$)alkoxycarbonyl, linear or branched ($C_1$–$C_6$)trihaloalkyl,
  amino optionally substituted by one or two groups, which may be identical or different, each independently of the other selected from linear or branched ($C_1$–$C_6$)alkyl, aryl, and aryl-($C_1$–$C_6$)alkyl in which alkyl is linear or branched,
  aryloxy, aryl-($C_1$–$C_6$)alkoxy in which alkoxy is linear or branched, heteroaryloxy, heteroaryl-($C_1$–$C_6$) alkoxy in which alkoxy is linear or branched,
  and a group of formula —$U_1$—$V_1$—$U_2$—$V_2$ wherein $U_1$, $U_2$, $V_1$ and $V_2$ are as defined hereinbefore,
  or two of them together form methylenedioxy, or ethylenedioxy each of those groups being optionally substituted by one or two linear or branched ($C_1$–$C_6$) alkyl, aryl, or aryl-($C_1$–$C_6$)alkyl in which alkyl is linear or branched,
- $R_1$ represents:
  aryl substituted by from one to five, identical or different, substituents each independently of the others selected from halogen, hydroxy, cyano, nitro, carboxy, linear or branched ($C_1$–$C_6$)alkyl, linear or branched ($C_1$–$C_6$)alkoxy, linear or branched ($C_1$–$C_6$) acyl, linear or branched ($C_1$–$C_6$)alkoxycarbonyl, linear or branched ($C_1$–$C_6$)trihaloalkyl (optionally substituted by hydroxy), linear or branched ($C_1$–$C_6$) trihaloalkoxy, amino (optionally substituted by one or two, linear or branched ($C_1$–$C_6$)alkyl, one of which alkyl may be optionally substituted by a group selected from amino, linear or branched ($C_1$–$C_6$) alkylamino, and di-($C_1$–$C_6$)alkylamino in which each alkyl are each linear or branched), amino-($C_1$–$C_6$)alkoxy (in which alkoxy is linear or branched, and amino is optionally substituted by one or two, identical or different, linear or branched ($C_1$–$C_6$)alkyl), ($C_1$–$C_6$)alkoxycarbonyl($C_1$–$C_6$)alkyl in which each alkoxy and alkyl are each linear or branched, linear or branched ($C_1$–$C_6$) alkylcarbonylamino, aryl-($C_1$–$C_6$)alkyl in which each alkyl is linear or branched, aryloxy, aryl-($C_1$–$C_6$)alkoxy in which alkoxy is linear or branched, arylamino, aryl-($C_1$–$C_6$)alkylamino in which each alkyl is linear or branched, arylsulphanyl, aryl-($C_1$–$C_6$)alkylsulphanyl in which each alkyl is linear or branched, heteroaryl, heteroaryl-($C_1$–$C_6$)alkyl in which each alkyl is linear or branched, heteroaryloxy, heteroaryl-($C_1$–$C_6$) alkoxy in which each alkoxy is linear or branched, heteroarylamino, heteroaryl-($C_1$–$C_6$)alkylamino in which each alkyl is linear or branched, heteroarylsulphanyl, heteroaryl-($C_1$–$C_6$) alkylsulphanyl in which each alkyl is linear or branched,
  1,3-dihydro-2H-indol-2-one, 3,4-dihydro-2(1H)-quinolinone, 1-hydroxy-2(1H)-pyridinone,
  or optionally substituted heteroaryl,
- $R_2$ represents a group selected from hydrogen, linear or branched ($C_1$–$C_6$)alkyl, aryl, aryl-($C_1$–$C_6$)alkyl in which each alkyl is linear or branched, cycloalkyl, heterocycloalkyl, heterocycloalkyl-($C_1$–$C_6$)alkyl in which each alkyl is linear or branched, heteroaryl, and heteroaryl-($C_1$–$C_6$)alkyl in which each alkyl is linear or branched, wherein:
aryl is understood to be phenyl, biphenyl, naphthyl, tetrahydronaphthyl, or dihydronaphthyl, each of those groups being optionally substituted by one or more, identical or different, groups selected from halogen, hydroxy, cyano, nitro, linear or branched ($C_1$–$C_6$)alkyl (optionally substituted by one or more groups selected from hydroxy, amino, mono ($C_1$–$C_6$) alkylamino and di-($C_1$–$C_6$)alkylamino in which each alkyl is each linear or branched), linear or branched ($C_1$–$C_6$)trihaloalkyl, linear or branched ($C_1$–$C_6$) alkoxy, aryloxy, linear or branched ($C_1$–$C_6$)acyl, carboxy, linear or branched ($C_1$–$C_6$)alkoxycarbonyl, and amino (amino being optionally substituted by one or two, identical or different, linear or branched ($C_1$–$C_6$)alkyl),
cycloalkyl is understood to be a mono- or bi-cyclic group containing from 3 to 8 atoms carbon,
heterocycloalkyl is understood to be mono- or bi-cyclic, saturated, or unsaturated group, of non-aromatic character, having from 5 to 12 ring members containing one, two, or three, identical or different, hetero atoms selected from oxygen, nitrogen, and sulphur, it being understood that heterocycloalkyl may be optionally substituted by one or more, identical or different, groups selected from halogen, hydroxy, linear or branched ($C_1$–$C_6$)alkyl, linear or branched ($C_1$–$C_6$)trihaloalkyl, linear or branched ($C_1$–$C_6$)alkoxy, aryloxy, aryl-($C_1$–$C_6$) alkoxy in which alkoxy is linear or branched, amino (optionally substituted by one or two linear or branched ($C_1$–$C_6$)alkyl), linear or branched ($C_1$–$C_6$) acyl, linear or branched ($C_1$–$C_6$)alkoxycarbonyl, nitro, and oxo,
heteroaryl is understood to be mono-, or bi-cyclic heterocycloalkyl as defined hereinbefore, at least one of the rings of which has aromatic character, it being possible for hetero atom(s) to be located, in the case of bicyclic system, on the ring having aromatic character or on the partially unsaturated ring, it being understood that heteroaryl may be optionally substituted by one or more, identical or different, groups as defined for the substituents of heterocycloalkyl,
its optical isomers, and pharmaceutically-acceptable acid or base addition salts thereof.

2. A compound of claim 1, wherein Y represents oxygen.

3. A compound of claim 1, wherein $R_1$ represents a group selected from phenyl optionally substituted by a group as defined in claim 1, optionally substituted quinolyl, and optionally substituted pyridyl.

4. A compound of claim 1, wherein $R_2$ represents a group selected from aryl, and heteroaryl, each of those groups being optionally substituted.

5. A compound of claim 1, wherein $R_2$ represents pyridyl.

6. A compound of claim 1, wherein $U_1$ represents linear ($C_1$–$C_4$)alkylene wherein one of carbon is replaced by oxygen, $V_1$ represents arylene, $U_2$ represents single bond, and $V_2$ represents aryl optionally substituted by one of the groups as defined in claim 1.

7. A compound of claim 1, wherein —$U_1$—$V_1$—$U_2$—$V_2$ represents [1,1'-biphenyl]-4-ylmethoxy.

8. A compound of claim 1, wherein at least one of the groups Ra, Rb, or Rc represents a group of formula —$U_1$—$V_1$—$U_2$—$V_2$.

9. A compound of claim 1, wherein X represents sulphur, Y represents oxygen, $R_1$ represents optionally substituted phenyl, or optionally substituted pyridyl, and A represents single bond, when T represents carbon or CH.

10. A compound of claim 1, wherein X represents sulphur, Y represents oxygen, $R_1$ represents phenyl optionally substituted by a group as defined in claim 1, and A represents alkylene (optionally substituted by linear or branched ($C_1$–$C_6$)alkyl, aryl, or aryl-($C_1$–$C_6$)alkyl in which alkyl is linear or branched), or arylene when T represents nitrogen.

11. A compound selected from those of claim 1, wherein it represents a compound of formula (II):

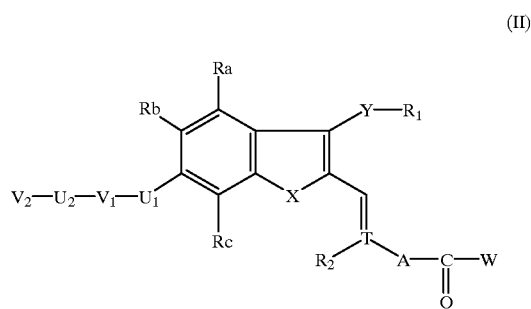

(II)

wherein:
X represents sulphur,
Y represents oxygen,
$R_1$ represents optionally substituted phenyl, or a heteroaryl group selected for quinolyl optionally substituted pyridyl,
A represents single bond,
T represents carbon,
Ra and Rc each represents hydrogen,
$U_1$ represents linear ($C_1$–$C_4$)alkylenoxy,
$V_1$ represents arylene,
$U_2$ represents single bond,
$V_2$ represents aryl,
Rb represents $U_1$—$V_1$—$U_2$—$V_2$ group as defined hereinbefore,
$R_2$ represents heteroaryl, and
W represents group as defined in claim 1, its optical isomers, and pharmaceutically-acceptable acid or base addition salts thereof.

12. A compound of claim 11, wherein Rb and —$U_1$—$V_1$—$U_2$—$V_2$ each represents [1,1'-biphenyl]-4-ylmethoxy group.

13. A compound of claim 11, wherein $R_2$ represents pyridyl.

14. A compound of claim 11, wherein $R_1$ represents:
phenyl optionally substituted by one to three groups selected from halogen, linear or branched ($C_1$–$C_6$) alkyl, heteroaryl, heteroaryl-($C_1$–$C_6$)alkoxy in which each alkoxy is linear or branched, linear or branched ($C_1$–$C_6$)alkoxy, amino, and linear or branched amino-($C_1$–$C_6$)alkoxy, in which each amino moiety is optionally substituted by one or two, identical or different, linear or branched ($C_1$–$C_6$)alkyl,
or heteroaryl selected from pyridyl and quinolyl optionally substituted by halogen, or linear or branched ($C_1$–$C_6$)alkyl.

15. A compound of claim 1 which is (E)-3-[5,6-bis([1,1'-biphenyl]-4-ylmethoxy)-3-(4-chlorophenoxy)benzo[b] thiophen-2-yl]-2-(4-pyridyl)-2-propenoic acid, its isomers, and pharmaceutically-acceptable acid or base addition salts thereof.

16. Compounds of claim 1 selected from:

ethyl (E)-3-[5,6-bis-([1,1'-biphenyl]-4-ylmethoxy)-3-(4-chlorophenoxy)-benzo[b]thiophen-2-yl]-2-(4-pyridyl)-2-propenoate, (E)-3-[5,6-bis-([1,1'-biphenyl]-4-ylmethoxy)-3-(3-pyridyloxy)-benzo[b]thiophen-2-yl]-2-(4-pyridyl)-2-propenoic acid, 3-(E)-{5,6-bis-([1,1'-biphenyl]-4-ylmethoxy)-3-[6-(methyl)pyridyl-3-oxy]-benzo[b]thiophen-2-yl}-2-(4-pyridyl)-2-propenoic acid, 3-(E)-[5,6-bis-([1,1'-biphenyl]-4-ylmethoxy)-3-(6-quinolyloxy)benzo[b]thiophen-2-yl]-2-(4-pyridyl)-2-propenoic acid, (E)-3-[5,6-bis-([1,1'-biphenyl]-2-ylmethoxy)-3-(4-chlorophenoxy)benzo[b]thiophen-2-yl]-2-(4-pyridyl)-2-propenoic acid, (E)-3-[5,6-bis([1,1'-biphenyl]-3-ylmethoxy)-3-(4-chlorophenoxy)-benzo[b]thiophen-2-yl]-2-(4-pyridyl)-2-propenoic acid, (E)-3-[5,6-bis([1,1'-biphenyl]-4-ylmethoxy)-3-(4-chloro-3-fluorophenoxy)-benzo[b]-thiophen-2-yl]-2-(4-pyridyl)-2-propenoic acid, (E)-3-[5,6-bis([1,1'-biphenyl]-4-ylmethoxy)-3-(4-chloro-3,5-dimethylphenoxy)-benzo[b]thiophen-2-yl]-2-(4-pyridyl)-2-propenoic acid, (E)-3-[5,6-bis([1,1'-biphenyl]-4-ylmethoxy)-3-(4-chloro-3-methylphenoxy)-benzo[b]-thiophen-2-yl]-2-(4-pyridyl)-2-propenoic acid, (E)-3-{5,6-bis([1,1'-biphenyl]-4-ylmethoxy)-3-[4-(4-pyridyloxy)phenoxy]-benzo[b]thiophen-2-yl}-2-(4-pyridyl)-2-propenoic acid, (E)-3-{5,6-bis([1,1'-biphenyl]-4-ylmethoxy)-3-[4-(1H-imidazol-1-yl)phenoxy]-benzo[b]thiophen-2-yl}-2-(4-pyridyl)-2-propenoic acid, (E)-3-[5,6-bis([1,1'-biphenyl]-4-ylmethoxy)-3-phenoxy-benzo[b]thiophen-2-yl]-2-(4-pyridyl)-2-propenoic acid, (E)-3-[5,6-bis([1,1'-biphenyl]-4-ylmethoxy)-3-(3-fluorophenoxy)-benzo[b]thiophen-2-yl]-2-(4-pyridyl)-2-propenoic acid, (E)-3-[5,6-bis([1,1'-biphenyl]-4-ylmethoxy)-3-(3,4-difluorophenoxy)-benzo[b]thiophen-2-yl]-2-(4-pyridyl)-2-propenoic acid, and (E)-3-{5,6-bis([1,1'-biphenyl]-4-ylmethoxy)-3-[(6-chloro-3-pyridyl)oxy]-benzo[b]thiophen-2-yl}-2-(4-pyridyl)-2-propenoic acid, its optical isomers, and pharmaceutically-acceptable acid or base addition salts thereof.

17. A method for treating a living body afflicted with a condition selected from thrombosis, pathologies for which the origin is thrombosis, or pathologies causing an increase in risk of thrombosis, comprising the step of administering to the living body in need thereof a compound of claim 1 in an amount effective to inhibit PAI-1 for alleviation of said condition.

18. A pharmaceutical composition useful comprising a compound as claimed in claim 1, in combination with one or more pharmaceutically-acceptable excipients or carriers.

* * * * *

UNITED STATES PATENT AND TRADEMARK OFFICE
CERTIFICATE OF CORRECTION

PATENT NO. : 6,302,837 B1  Page 1 of 1
DATED : October 16, 2001
INVENTOR(S) : Guillaume De Nanteuil et al.

It is certified that error appears in the above-identified patent and that said Letters Patent is hereby corrected as shown below:

Title page,
Item [74] *Attorney, Agent, or Firm*: "Hueschena" should read -- Hueschen --.

Column 29,
Line 22, "when bond" should read -- when the bond --.

Column 30,
Line 36, "are" should read -- is --

Column 34,
Line 26, please delete "useful", which should have been deleted in the Examiners Amendment.

Signed and Sealed this

Twenty-eighth Day of May, 2002

Attest:

JAMES E. ROGAN
*Attesting Officer*  *Director of the United States Patent and Trademark Office*